(12) United States Patent
Kolter et al.

(10) Patent No.: US 6,635,279 B2
(45) Date of Patent: Oct. 21, 2003

(54) ACTIVE INGREDIENT-CONTAINING FLOATING FORMS COMPRISING POLYVINYL ACETATE AND POLYVINYLPYRROLIDONE, THEIR USE AND PRODUCTION

(75) Inventors: Karl Kolter, Limburgerhof (DE); Michael Schönherr, Frankenthal (DE); Hermann Ascherl, Dirmstein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 7 days.

(21) Appl. No.: 09/811,434

(22) Filed: Mar. 20, 2001

(65) Prior Publication Data

US 2003/0021846 A1 Jan. 30, 2003

(30) Foreign Application Priority Data

Mar. 27, 2000 (DE) .......................... 100 14 588

(51) Int. Cl.⁷ ............................. A61K 9/22; A61K 9/24; A61K 9/28; A61K 9/52
(52) U.S. Cl. ....................... 424/468; 424/465; 424/457; 424/470; 424/472; 424/474
(58) Field of Search ................................. 424/464, 465, 424/457, 474, 472, 470, 468

(56) References Cited

U.S. PATENT DOCUMENTS

| 4,101,650 A | 7/1978 | Umezawa |
| 4,126,672 A | 11/1978 | Sheth et al. |
| 4,140,755 A | 2/1979 | Sheth et al. |
| 4,167,558 A | 9/1979 | Sheth et al. |
| 4,424,235 A | 1/1984 | Sheth et al. |
| 4,702,918 A | 10/1987 | Ushimaru et al. |
| 4,767,627 A | 8/1988 | Caldwell et al. |
| 4,814,179 A | 3/1989 | Bolton et al. |
| 4,851,232 A | 7/1989 | Urquhart |
| 4,871,548 A | 10/1989 | Edgren et al. |
| 5,007,790 A | 4/1991 | Shell |
| 5,169,638 A | 12/1992 | Dennis et al. |
| 5,232,704 A | 8/1993 | Franz et al. |
| 5,343,147 A | 8/1994 | Sager et al. |
| 5,443,843 A | 8/1995 | Curatolo et al. |
| 5,490,990 A | 2/1996 | Grabowski et al. ......... 424/486 |
| 5,582,873 A | 12/1996 | Desai |
| 5,626,876 A | 5/1997 | Muller et al. |
| 5,651,985 A | 7/1997 | Penners et al. ............. 424/469 |
| 6,066,334 A * | 5/2000 | Kolter et al. ............... 424/465 |

FOREIGN PATENT DOCUMENTS

| CA | 2213511 | 8/1996 |
| DE | 35 27 852 | 2/1986 |
| EP | 198 769 | 10/1986 |
| EP | 235 718 | 9/1987 |
| EP | 326 816 | 8/1989 |
| EP | 0 575 930 | 12/1993 |
| EP | 0 669 129 | 8/1995 |
| GB | 2 283 171 | 5/1995 |
| GB | 2 283 172 | 5/1995 |
| WO | 95/05809 | 3/1995 |
| WO | 96/25950 | 8/1996 |
| WO | 99/07342 | 2/1999 |
| WO | 99/45887 | 9/1999 |

* cited by examiner

*Primary Examiner*—James M. Spear
(74) *Attorney, Agent, or Firm*—Keil & Weinkauf

(57) ABSTRACT

The present invention relates to oral dosage forms comprising a) one or more active ingredients b) a formulated mixture of polyvinyl acetate and polyvinylpyrrolidone c) where appropriate other excipients customary for producing the dosage form, wherein they float on gastric fluid and display delayed release of active ingredient, and to the use and production thereof.

22 Claims, No Drawings

ACTIVE INGREDIENT-CONTAINING FLOATING FORMS COMPRISING POLYVINYL ACETATE AND POLYVINYLPYRROLIDONE, THEIR USE AND PRODUCTION

The present invention relates to active ingredient-containing dosage forms comprising polyvinyl acetate and polyvinylpyrrolidone which float on gastric fluids after intake and thus result in delayed release of active ingredient. These forms can be produced by simple processes and exhibit exceptional mechanical strengths.

Slow-release dosage forms are becoming increasingly important, firstly because the frequency of administration can be reduced, and secondly because they lead to a reduction in the fluctuations in the levels in the blood. The lower maximum level in the blood may reduce the severity of dose-dependent side effects and thus, for example for drug products, improve the tolerability. The higher minimum plasma concentration increases the efficacy, especially of active ingredients for which the concentration ought not to fall below a particular threshold.

After intake of the slow-release dosage form it reaches the stomach, where it is normally transported after 0.5–3 h into the small intestine. The time to pass through the small intestine is usually 3–6 h. The result of this is that absorption of the active ingredient must be complete within about 3–6 h because most active ingredients are absorbed in the colon to only a negligible extent or not at all. It is therefore possible to adjust a longer release-slowing period only with difficulty. The bioavailability of active ingredients which are not completely absorbed in this period decreases because part of the dose is lost. An additional factor is that certain active ingredients have an absorption window, which is very quickly passed through with conventional dosage forms, in the small intestine.

A system which remains in the stomach for a longer time and continuously releases active ingredient would avoid these disadvantages, since the active ingredient would continuously pass through the pylorus in dissolved form and could be taken up in the small intestine. It is possible in this way on the one hand to extend the bioavailability but also, on the other hand, to extend the duration of action, for example of a drug product.

In addition, there are some active ingredients intended to act locally in the stomach. An extended duration of action is frequently desired for these too.

There have been frequent approaches to extending the residence time by tablets which swell in the stomach and become so large that they are no longer able to pass through the pylorus. Such forms are described in U.S. Pat. Nos. 4,871,548; 4,767,627; 5,443,843; 5,007,790; 5,582,873; 4,851,232; WO 99/07342. In most of these, hydroxyalkylated celluloses are used as swelling agents. All these forms have the disadvantage that they may block the outlet from the stomach and may cause health problems. In addition, the swelling depends greatly on the contents of the stomach and the osmolarity of the medium. These eventually also influence the release-slowing action and the residence time.

Another possibility for extending the residence time in the stomach is to produce floating forms. These float on the contents of the stomach and, because the pylorus is located in the lower part of the stomach, are not discharged into the small intestine for a lengthy period.

Various processes are known for producing such forms. Thus, it is possible to incorporate substances which have per se a low density, such as, for example, fats, oils or waxes. Such forms are described in the Applications EP 198769 (Forest Laboratories Inc.), U.S. Pat. No. 4,424,235, U.S. Pat. No. 8,343,47, U.S. Pat. No. 3,014,98, BE 839604 (Hoffmann-LaRoche). However, relatively large amounts are necessary for this and increase the volume of the dosage forms and make them more difficult to swallow and, in addition, these substances have a very disadvantageous effect on the strength of the shaped products. Compression results in tablets with low hardnesses, and the tablets frequently adhere to the punch during production. The Application DE 3527852 (Nippon Shinyaku KK) describes fat-containing mixtures which are packed into a capsule and must be heated for solidification. This is complicated and entirely unsuitable for temperature-labile active ingredients. Shaped articles are produced in the US Application U.S. Pat. No. 4,814,179 (Univ. of St.Johns) by cooling and gelling and drying. This process is even more elaborate.

Another method makes use of the evolution of gas from salts of carbonic acid. This entails these salts being incorporated together with gel formers into the dosage forms and, after exposure to gastric acid, $CO_2$ is produced and inflates the form and leads to the floating. In order to be independent of gastric acid there is frequently incorporation of physiologically tolerated acids such as, for example, citric acid or tartaric acid. These preparations are very sensitive to moisture, so that humidity must be low during production and no water-containing excipients can be employed. The packaging material for the dosage forms must be very leakproof so that the forms do not effervesce even during storage. The evolution of gas on contact with acid often also affects the structure of the dosage forms and the release-slowing effect is reduced. Since these preparations are often difficult to compress, and tablets with adequate mechanical stability are not obtained, such preparations are frequently and inconveniently packed in hard or soft gelatin capsules. Examples thereof are described in the Applications GB 2283172 (Scherer LTD), GB 2283171 (Reckitt & Colman Prod LTD).

The production of tablets is described in WO 99/45887 (Temple Univ), U.S. Pat. No. 4,167,558 (Hoffmann-LaRoche), and the production of two-layer tablets is described in U.S. Pat. No. 4,140,755 (Hoffmann-LaRoche). Besides the disadvantages already mentioned above, with these tablets there are enormous problems with reproducibility of the release. It is generally known that the gel-forming capacity and the gel strength of polysaccharides varies from batch to batch because of the variation in the chain length and the degree of substitution, and this is exacerbated by the disturbance of the gel structure through evolution of $CO_2$. In addition, the gel formers react very sensitively to differences in the osmolarity of the release media, with alterations in the release.

Even more delicate and complicated are preparations in which coating layers are applied to a core able to evolve $CO_2$. In some cases, the coating itself contains a salt of carbonic acid. These coatings must be applied using organic solvents. Such preparations are described in EP 235718 (Eisai KK), US 4,101,650 (Microbiochemical Research Foundation), WO 99/49868 (Yuhan Corp).

A powder which comprises active ingredient, hydrocolloid, pH-dependent polymer and binder and is packed into a capsule is described in U.S. Pat. No. 5,169,638 (Squibb & Sons Inc). However, the gelling and release depend very greatly on the surrounding conditions.

U.S. Pat. No. 5,232,704 describes forms consisting of 2 layers, one of which contains active ingredient and the other is responsible for the floating. The production is elaborate and high-dose drugs cannot be processed.

Aerogels, foams and air-containing microcapsules are likewise described in WO 96/25950 (Hoechst AG), EP 326816 (LTS Lohmann), WO 95/05809 (Nippon Shinyaku), but the disadvantage of these microcapsules is often that the substances are not pharmaceutically approved, very complicated to process or difficult to tablet. The lyophilization of active ingredients or additives to produce a porous shaped article is enormously time-consuming and costly.

Using porous shaped articles as starting material and applying active ingredient or other excipients thereto increases the volume of the dosage form correspondingly.

The use of solvents in the production moreover increases costs and, in addition, is not environmentally friendly.

It is an object of the present invention to develop a suitable composition for a slow-release dosage form which does not have the abovementioned disadvantages.

We have found that this object is achieved by an oral dosage form comprising a) one or more active ingredients b) a formulated mixture of polyvinyl acetate and polyvinylpyrrolidone c) where appropriate other excipients customary for producing the dosage form, wherein it floats on gastric fluid and displays delayed release of active ingredient.

The dosage forms are preferably employed for active pharmaceutical ingredients.

However, they can also be employed for any other active ingredient for which delayed release is desired.

These forms can be produced by simple processes and display exceptional mechanical strengths. Surprisingly, it is possible to produce floating forms with delayed release from polyvinyl acetate and polyvinylpyrrolidone although N. Rouge, E. T. Cole, E. Doelker and P. Buri, S. T. P. Pharma Sciences 7(5), 386–92 (1997) found that floating forms cannot be produced by compression with inert matrix formers such as ethylcellulose and cellulose acetate. Only swelling matrix formers were capable of this. Polyvinyl acetate and polyvinylpyrrolidone likewise form inert matrices on compression, i.e. no swelling and erosion takes place in gastric or intestinal fluid.

The exceptionally good compressibility of this combination makes it possible to produce very mechanically stable oral dosage forms, in particular tablets with great slowing of release even with extremely low pressures. The plastic behavior of this combination leads to retention of high porosity, resulting in the dosage forms floating on gastric fluid. Although it was normally to be expected that the large pore volume will lead to rapid release, there is a potent release-slowing effect despite the high porosity.

Even after penetration of gastric fluid, the dosage forms float for up to 48 h and do not sink, despite the increase in weight arising therefrom.

Surprisingly, the polyvinyl acetate/polyvinylpyrrolidone combination combines the following properties:

1. Buoyancy through generation of a high porosity in the tablet
2. Binding effect, usually making an additional binder unnecessary
3. Flow aid effect because it greatly improves the flowability of powder mixtures
4. Release-slowing effect.

The ratio of polyvinyl acetate to polyvinylpyrrolidone is preferably between 6:4 and 9:1, and is particularly preferably 8:2.

Combination of these various effects often means that no other excipients are necessary in the dosage form, or the amount thereof can be chosen to be very small. The consequence is a very small form in terms of volume, making oral administration easily possible.

Incorporation of salts of carbonic acid is unnecessary, nor is that of other porous shaped articles, hollow beads etc. It is, of course, possible for these substances to be incorporated in principle, in which case the amounts should be small because with larger amounts, especially of carbonic acid salts, the structure may be harmed. The amount of carbonic acid salts should be below 10%, preferably below 5%, and that of porous shaped articles should be below 30%, preferably below 20%.

The floating dosage forms are produced most simply by direct tableting, for which purpose often only the active ingredient, the combination of polyvinyl acetate and polyvinylpyrrolidone and a lubricant are necessary. The formula is simple, very reproducible and very robust. It is, of course, also possible to add other conventional tableting excipients, for example flow regulators, binders, disintegrants, colorants or bulking agents. To mask an unpleasant taste or odor it is possible to add flavorings or sweeteners.

Lubricants which can be used are stearates of aluminum, calcium, magnesium and tin, and magnesium silicate, silicones and the like.

Examples of possible flow aids are talc, colloidal silica, starch or free-flowing microcrystalline cellulose.

Examples of binders are starch, alginates, carboxymethylcellulose or polyvinylpyrrolidone. Possible disintegrants are starch or starch paste or microcrystalline cellulose. Stabilizers.

Bulking agents which can be added are, for example, inorganic bulking agents such as oxides of magnesium, aluminum, silicon, or titanium carbonate or calcium carbonate.

Examples of colorants are iron oxides, titanium dioxide, triphenylmethane dyes, azo dyes, quinoline dyes, indigotine dyes, carotenoids, for coloring the dosage forms, opacifying agents such as titanium dioxide or talc to increase the transparency to light and to save on colorants.

It is also possible to use dry granulation processes and wet granulation processes. Care must be taken in this connection that the chosen processes do not lead to great compaction. Thus, fluidized bed granulation is ideal for this purpose because of the small mechanical energy input.

The dosage forms according to the invention are suitable for use in oral dosage forms such as tablets or capsules, preferably for producing tablets.

To produce mechanically stable tablets it is normally necessary to use pressures of 150–800 MPa. The pressures required to produce the floating forms are below 100, preferably below 60, MPa. With conventional tableting excipients under so much lower pressures either no tablets are produced—the compressed material emerges as powder from the die—or the strengths of the tablet are so low that it cannot be further processed. Tablets must be sufficiently stable to survive a coating process and packaging without harm. This is usually the case when the strength, based on the fracture area, exceeds 1 $N/mm^2$, preferably 2 $N/mm^2$, and the friability is less than 2.0%, preferably less than 1.0%.

In the development of the floating forms, the pressure is increased until, on the one hand, the tablet still floats but also, on the other hand, the hardness is maximized and the friability is low. The friability should be less than 3%, preferably less than 1.5%, particularly preferably less than 1%.

Elaborate processes such as lyophilization, coating of tablet ingredients or steps using organic solvents are unnecessary.

The tablets compressed in this way can also be introduced in the form of microtablets into capsules.

The dosage forms according to the invention may comprise any active ingredient for which delayed release is desired.

The active ingredients preferably employed are food supplements or additives, vitamins, minerals or trace elements, but particularly preferably active pharmaceutical ingredients.

Pharmaceutical formulations of the abovementioned type can be obtained by processing the claimed compounds with active pharmaceutical ingredients by conventional methods and with use of known and novel active ingredients. The active ingredients may moreover come from any area of indications.

Examples which may be mentioned here are the following:

benzodiazepines, antihypertensives, vitamins, cytostatics, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents and other antihyperkinetics, ophthalmologicals, neuropathy products, calcium metabolism regulators, muscle relaxants, lipid-lowering agents, liver therapeutics, coronary agents, cardiac agents, immunotherapeutics, regulatory peptides and their inhibitors, hypnotics, sedatives, gynecologicals, antigout agents, fibrinolytics, enzyme products and transport proteins, enzyme inhibitors, emetics, perfusion promoters, diuretics, diagnostics, corticoids, cholinergics, biliary therapeutics, antiasthmatics, bronchiospasmolytics, beta-receptor blockers, calcium channel blockers, ACE inhibitors, arteriosclerosis remedies, antiinflammatory agents, anticoagulants, antihypotensives, antihypoglycemics, antifibrinolytics, antiepileptics, antiemetics, antidotes, antidiabetics, antiarrhythmics, antianemics, antiallergics, anthelmintics, analgesics, analeptics, aldosterone antagonists, weight-reducing agents.

The release of active ingredient is adjusted by the amount of polyvinyl acetate/polyvinylpyrrolidone. Release is slowed by larger amounts of the combination. The proportionate amounts necessary for floating and delayed release are between 10 and 99%, preferably between 20 and 70%, based on the total weight of the tablet. Besides the formulated mixture of polyvinyl acetate and polyvinylpyrrolidone it is also possible to employ other release-slowing excipients before or after the granulation.

The release can be speeded up by adding polymers which are freely soluble in water; however, it can also be slowed down by adding substances which are very lipophilic or swell in water. The latter lead to gel formation in the pores of the inert matrix and thus prevent diffusion of the drug outwards. Examples of such gel formers are alginates, pectins, galactomannans, carrageenans, dextran, curdlan, pullulan, gellan, chitin, gelatin, xanthans, hemicelluloses, cellulose derivatives such as methylcellulose, hydroxypropylmethylcellulose, hydroxypropylcellulose, hydroxyethylcellulose, carboxymethylcellulose, starch derivates such as carboxymethyl starch, degraded starch, maltodextrins, polyacrylic acid, polymethacrylic acid, acrylic acid/methacrylic acid copolymers, polyvinyl alcohols, high molecular weight polyethylene glycols, polyoxyethylene/polyoxypropylene block copolymers, high molecular weight polyvinylpyrrolidones and derivatives thereof.

The lipophilic substances include, for example, fatty alcohols such as stearyl alcohol, fatty acids such as stearic acid, glycerides, fatty acid esters and fatty alcohol esters, lipophilic polymers such as ethylcellulose, cellulose acetate, acrylic ester/methacrylic ester copolymers, methacrylic acid/acrylic ester copolymers, cellulose acetate phthalate, cellulose acetate succinate, hydroxypropylmethylcellulose acetate phthalate, hydroxypropylmethylcellulose acetate succinate.

The water-soluble polymers include, for example, polyethylene glycols, polyvinylpyrrolidone or vinylpyrrolidone/vinyl acetate copolymers.

These additives can be employed in amounts of 0.1–30%, preferably 0.5–20%.

The shape of the tablet can be varied within wide limits. Thus, biconvex, biplanar, round or polygonal tablets can be produced, as well as oblong or football shapes. The upper limit on size is determined by the swallowability while the lower limit is determined by machine design limits. Conventional tablet sizes are between 1 and 16 mm, preferably between 2 and 13 mm diameter.

It is also possible to produce two-layer tablets in which one layer contains the complete dose of active ingredient or at least has a very large active ingredient content, whereas the other layer has a very large content of the polyvinyl acetate/polyvinylpyrrolidone combination. These two layers may also differ in their porosity. The layer with the large polyvinyl acetate/polyvinylpyrrolidone content is usually more porous and is then mainly responsible for the buoyancy.

A particular embodiment is the production of press-coated tablets in which the core has a very large active ingredient content or may even contain the complete amount of active ingredient, whereas the covering consists to a large extent of the polyvinyl acetate/polyvinylpyrrolidone combination. This produces a great slowing of release. This form is particularly suitable for active ingredients which are very freely soluble in water and are intended to be released very slowly.

The tablets according to the invention can also be produced by melt extrusion and subsequent calendering.

The tablets can be provided in a conventional way with a film coating. This coating may be soluble in water, and then it merely serves to improve the visual appearance or mask an unpleasant odor or taste, but it may also be insoluble in water, and then is used to reduce release of active ingredient further. This is necessary if a very long duration of action is desired. It is possible in principle to employ all pharmaceutically approved coating materials, for example hydroxypropylmethylcellulose (Pharmacoat 603 or 606, supplied by Shin-Etsu), hydroxypropylcellulose, ethylcellulose, cellulose acetate phthalate, ammoniomethacrylate copolymer (USP), methacrylic acid copolymer type C (USP), butyl methacrylate/2-dimethylaminoethyl methacrylate/methyl methacrylate copolymer, polyvinyl acetate, polyvinylpyrrolidone.

The following examples are intended to illustrate the invention in detail without, however, restricting it thereto.

EXAMPLE 1

Floating Caffeine Tablet 1.6 kg of caffeine, 1.6 kg of formulated mixture of polyvinyl acetate and polyvinylpyrrolidone in the ratio 8:2 (Kollidon SR) and 0.02 kg of magnesium stearate were passed through a 0.8 mm sieve, mixed in a Turbula mixer for 10 min and compressed in a Korsch EKO eccentric tablet press to biplanar tablets with a diameter of 10 mm and a weight of 322 mg. The compressive force was 2.04 kN.

The following data were determined for the powder and tablets:

| | |
|---|---|
| Angle of repose: | 23° |
| Flow time: | 7.7 s |
| Hardness: | 54 N |
| Friability: | 0.94% |

The tablets floated immediately after addition to simulated gastric fluid. The floating persisted for 48 h (Table 1).

TABLE 1

Release from floating caffeine tablets

| Time [h] | Amount of active ingredient released [%] |
|---|---|
| 0 | 0.0 |
| 0.5 | 25.6 |
| 1 | 39.4 |
| 1.5 | 53.1 |
| 2 | 61.5 |
| 3 | 71.9 |
| 4 | 80.6 |
| 6 | 96.3 |
| 8 | 100.9 |
| 12 | 103.0 |
| 16 | 103.3 |

EXAMPLE 2

Floating Diltiazem Tablet 1.2 kg of diltiazem HCl, 2.0 kg of formulated mixture of polyvinyl acetate and polyvinylpyrrolidone in the ratio 8:2 (Kollidon SR), 0.03 kg of Aerosil 200 and 0.03 kg of magnesium stearate were passed through a 0.8 mm sieve, mixed in a Turbula mixer for 10 min and compressed in a Korsch PH 106 rotary tablet press to biplanar tablets with a diameter of 10 mm and a weight of 326 mg. The compressive force was 3.76 kN.

The following data were found for the powder and tablets:

| | |
|---|---|
| Angle of repose: | 29° |
| Flow time: | 15.5 s |
| Hardness: | 111 N |
| Friability: | 0.26% |

The tablets floated immediately after addition to simulated gastric fluid. The floating was maintained for 48 h (Tables 2–4).

TABLE 2

Release from floating diltiazem HCl tablets

| Time [h] | Amount of active ingredient released [%] | | | |
|---|---|---|---|---|
| 0 | 0 | 0 | 0 | 0 |
| 0.5 | 15.9 | 16.3 | 15.5 | 15.4 |
| 1 | 24.5 | 24.4 | 22.1 | 22.3 |
| 1.5 | 32.2 | 29.4 | 30.4 | 30.1 |
| 2 | 37.8 | 37.6 | 36.3 | 35.7 |
| 3 | 44.8 | 44.9 | 43.1 | 42.7 |
| 4 | 54.1 | 50.9 | 48.7 | 48.6 |
| 6 | 64.0 | 60.5 | 58.9 | 56.7 |
| 8 | 70.9 | 69.3 | 66.2 | 64.7 |
| 12 | 82.8 | 83.3 | 76.8 | 74.8 |
| 16 | 92.5 | 91.6 | 85.9 | 87.6 |

TABLE 3

Release of the active ingredient from floating diltiazem HCl tablets with different compressive forces

| Time [h] | Amount of active ingredient released [%] | | | |
|---|---|---|---|---|
| 0 | 0 | 0 | 0 | 0 |
| 0.5 | 15.9 | 16.3 | 15.5 | 15.4 |
| 1 | 24.5 | 24.4 | 22.1 | 22.3 |
| 1.5 | 32.2 | 29.4 | 30.4 | 30.1 |
| 2 | 37.8 | 37.6 | 36.3 | 35.7 |
| 3 | 44.8 | 44.9 | 43.1 | 42.7 |
| 4 | 54.1 | 50.9 | 48.7 | 48.6 |
| 6 | 64.0 | 60.5 | 58.9 | 56.7 |
| 8 | 70.9 | 69.3 | 66.2 | 64.7 |
| 12 | 82.8 | 83.3 | 76.8 | 74.8 |
| 16 | 92.5 | 91.6 | 85.9 | 87.6 |

TABLE 4

Hardness and effect of the compressive force on the floating behavior of floating diltiazem HCl tablets

| | Volume [mm$^3$] | Weight [mg] | Density [mg/mm$^3$] | Height [mm] | Compressive force [kN] |
|---|---|---|---|---|---|
| 2.1 | 434.0 | 331.0 | 0.76 | 5.65 | 1.85 |
| 2.2 | 400.3 | 323.6 | 0.81 | 5.22 | 2.36 |
| 2.3 | 373.6 | 338.1 | 0.91 | 4.88 | 2.94 |
| 2.4 | 348.5 | 337 | 0.97 | 4.56 | 3.76 |
| 2.5 | 339.0 | 335.2 | 0.99 | 4.44 | 4.11 |
| 2.6 | 327.3 | 336 | 1.03 | 4.29 | 4.79 |
| 2.7 | 304.5 | 332.7 | 1.09 | 4 | 6.61 |

| | | | | | | | | |
|---|---|---|---|---|---|---|---|---|
| Compressive force [kN] | 1.85 | 2.36 | 2.94 | 3.76 | 4.11 | 4.79 | 6.61 | 8 8.5 |
| Time until tablet floats [min] | 0.01 | 0.01 | 0.01 | 0.01 | 45 | 90 | 1440 | |
| Floating time [h] Volume [mm$^3$] | 60 | 60 | 60 | 60 | 60 | 60 | 60 | 0 0 |
| Hardness [N] | 23 | 43 | 84 | 111 | 117 | 152 | 203 | |

EXAMPLE 3

Floating Tramadol Tablet 1.0 kg of tramadol HCl, 1.5 kg of formulated mixture of polyvinyl acetate and polyvinylpyrrolidone in the ratio 8:2 (Kollidon SR), 0.1 kg of xanthan, 0.03 kg of Aerosil 200 and 0.03 kg of magnesium stearate were passed through a 0.8 mm sieve, mixed in a Turbula mixer for 10 min and compressed in a Korsch PH 106 rotary tablet press to biplanar tablets with a diameter of 10 mm and a weight of 276 mg. The compressive force was 3.76 kN.

The following data were found for the powder and tablets:

| | |
|---|---|
| Angle of repose: | 24.6° |
| Flow time: | 9.2 s |
| Hardness: | 62 N |
| Friability: | 0.24% |

The tablets floated immediately after addition to simulated gastric fluid. The floating was maintained for 48 h (Table 5).

TABLE 5

Tramadol release

| Time [h] | Amount of active ingredient released [%] |
|---|---|
| 0 | 0.0 |
| 0.5 | 25.6 |
| 1 | 39.4 |
| 1.5 | 53.1 |
| 2 | 61.5 |
| 3 | 71.9 |
| 4 | 80.6 |
| 6 | 96.3 |
| 8 | 100.9 |
| 12 | 103.0 |
| 16 | 103.3 |

EXAMPLE 4
Floating Propranolol HCl Tablet 1.6 kg of propranolol HCl and 1.6 kg of formulated mixture of polyvinyl acetate and polyvinylpyrrolidone in the ratio 8:2 (Kollidon SR) were passed through a 0.8 mm sieve and granulated in a fluidized bed granulator by spraying with 0.7 kg demineralized water at an inlet air temperature of 50° C. 0.03 kg of magnesium stearate was mixed into the dried granules in a Turbula mixer with a mixing time of 10 min. This mixture was compressed in a Korsch PH 106 rotary tablet press to biplanar tablets with a diameter of 10 mm and a weight of 320 mg. The compressive force was 3.14 kN.

The following data were found for the powder and tablets:

| | |
|---|---|
| Angle of repose: | 29.5° |
| Flow time: | 9.8 s |
| Hardness: | 59 N |
| Friability: | 0.49% |

The tablets floated immediately after addition to simulated gastric fluid. The floating was maintained for 48 h (Table 6).

TABLE 6

Release from floating propranolol tablets

| Time [h] | Amount of active ingredient released [%] |
|---|---|
| 0 | 0.0 |
| 0.5 | 21.5 |
| 1 | 31.2 |
| 1.5 | 37.5 |
| 2 | 42.8 |
| 3 | 49.5 |
| 4 | 57.8 |
| 6 | 73.0 |
| 8 | 83.5 |
| 12 | 92.7 |
| 16 | 97.5 |

EXAMPLE 5
Floating Diltiazem Coated Tablet 1.2 kg of diltiazem HCl, 2.0 kg of formulated mixture of polyvinyl acetate and polyvinylpyrrolidone in the ratio 8:2 (Kollidon SR) and 0.03 kg of magnesium stearate were passed through a 0.8 mm sieve, mixed in a Turbula mixer for 10 min and compressed in a Korsch PH 106 rotary tablet press to biconvex tablets with a diameter of 9 mm and a weight of 323 mg. The compressive force was 3.54 kN.

These tablet cores were coated in a horizontal drum coater (Accela Cota, from Manesty) with a solution of 160 g of hydroxypropylmethylcellulose (Pharmacoat 606) in 2.0 kg of demineralized water at an inlet air temperature of 50° C.

The following data were found for the tablets:

| | |
|---|---|
| Hardness: | 124 N |
| Friability: | 0.11% |

The tablets floated immediately after addition to simulated gastric fluid. The floating was maintained for 48 h.

EXAMPLE 6
Floating Theophylline Microtablets 1.6 kg of theophylline, 1.6 kg of formulated mixture of polyvinyl acetate and polyvinylpyrrolidone in the ratio 8:2 (Kollidon SR) and 0.02 kg of magnesium stearate were passed through a 0.8 mm sieve, mixed in a Turbula mixer for 10 min and compressed in a Korsch EKO eccentric tablet press to biconvex tablets with a diameter of 2 mm and a weight of 6 mg. The compressive force on use of a 5-fold tool was 0.4 kN. 50 microtablets were packed into a size 0 elongated capsule.

The tablets showed a friability of 0.5% and floated immediately after the capsule had dissolved on simulated gastric fluid. The floating was maintained for 24 h.

EXAMPLE 7
Floating Caffeine Tablet 1.6 kg of caffeine, 1.6 kg of formulated mixture of polyvinyl acetate and polyvinylpyrrolidone in the ratio 7:3, 0.2 kg of hydroxypropylmethylcellulose (Methocel K 100) and 0.02 kg of magnesium stearate were passed through a 0.8 mm sieve, mixed in a Turbula mixer for 10 min and compressed in a Korsch EKO eccentric tablet press to biplanar tablets with a diameter of 10 mm and a weight of 322 mg. The compressive force was 2.82 kN.

The following data were found for the powder and tablets:

| | |
|---|---|
| Angle of repose: | 28° |
| Flow time: | 13.6 s |
| Hardness: | 56 N |
| Friability: | 0.82% |

The tablets floated immediately after addition to simulated gastric fluid. The floating was maintained for 48 h.

EXAMPLE 8
Floating Diltiazem Tablet 1.6 kg of diltiazem HCl, 1.6 kg of formulated mixture of polyvinyl acetate and polyvinylpyrrolidone in the ratio 8:2, 0.03 kg of sodium bicarbonate, finely powdered, and 0.02 kg of magnesium stearate were passed through a 0.8 mm sieve, mixed in a Turbula mixer for 10 min and compressed in a Korsch EKO eccentric tablet press to biplanar tablets with a diameter of 10 mm and a weight of 325 mg. The compressive force was 4.15 kN.

The following data were found for the powder and tablets:

| | |
|---|---|
| Angle of repose: | 30° |
| Flow time: | 15.9 s |
| Hardness: | 139 N |
| Friability: | 0.09% |

The tablets floated immediately after addition to simulated gastric fluid. The floating was maintained for 48 h.

EXAMPLE 9

Floating Biperiden Tablet 0.04 kg of biperiden HCl, 1.6 kg of formulated mixture of polyvinyl acetate and polyvinylpyrrolidone in the ratio 8:2, 0.34 kg of microcrystalline cellulose and 0.02 kg of magnesium stearate were passed through a 0.8 mm sieve, mixed in a Turbula mixer for 10 min and compressed in a Korsch EKO eccentric tablet press to biplanar tablets with a diameter of 8 mm and a weight of 200 mg. The compressive force was 1.9 kN.

The following data were found for the powder and tablets:

| | |
|---|---|
| Angle of repose: | 24° |
| Flow time: | 7.3 s |
| Hardness: | 78 N |
| Friability: | 0.04% |

The tablets floated immediately after addition to simulated gastric fluid. The floating was maintained for 48 h.

COMPARATIVE EXAMPLE

Caffeine Tablet with Hydroxypropylmethylcellulose 1.6 kg of caffeine, 1.6 kg of hydroxypropylmethylcellulose (Methocel K 100) and 0.02 kg of magnesium stearate were passed through a 0.8 mm sieve, mixed in a Turbula mixer for 10 min and compressed in a Korsch EKO eccentric tablet press to biplanar tablets with a diameter of 10 mm and a weight of 322 mg. The compressive force was 2.06 kN.

The following data were found for the powder and tablets:

| | |
|---|---|
| Angle of repose: | 42° |
| Flow time: | flow stops |
| Hardness: | 7 N |
| Friability: | 100% (fracture) |

The tablets floated immediately after addition to simulated gastric fluid, but the mechanical properties are completely inadequate.

With a compressive force of 6.48 kN, the measured hardness was 49 N, but the tablets no longer float on simulated gastric fluid.

COMPARATIVE EXAMPLE

Caffeine Tablet with Acrylic Ester Copolymer 1.6 kg of caffeine, 1.6 kg Eudragit RS and 0.02 kg of magnesium stearate were passed through a 0.8 mm sieve, mixed in a Turbula mixer for 10 min and compressed in a Korsch EKO eccentric tablet press to biplanar tablets with a diameter of 10 mm and a weight of 322 mg. The compressive force was 3.03 kN.

The following data were found for the powder and tablets:

| | |
|---|---|
| Angle of repose: | 41° |
| Flow time: | 10.4 s |
| Hardness: | 5 N |
| Friability: | 100% (fracture) |

The tablets sink to the bottom immediately after addition to simulated gastric fluid, and the mechanical properties of the tablets are completely inadequate.

Even with a compressive force of 6.04 kN, the measured hardness was only 14 N.

We claim:

1. An oral dosage form comprising
   a) one or more active ingredients
   b) a formulated mixture of polyvinyl acetate and polyvinylpyrrolidone
   c) where appropriate other excipients customary for producing the dosage form,
   which floats on gastric fluid and displays delayed release of active ingredient, wherein the proportion of the formulated mixture of polyvinyl acetate and polyvinylpyrrolidone is between 20 and 70%, based on the total weight of the oral dosage form.

2. A dosage form as claimed in claim 1, wherein the ratio of polyvinyl acetate to polyvinylpyrrolidone is from 6:4 to 9:1.

3. A dosage form as claimed in claim 1, wherein the oral dosage form is a tablet, capsule or a coated tablet.

4. A dosage form as claimed in claim 1, wherein the dosage form is a tablet.

5. A dosage form as claimed in claim 1, wherein the release is adjusted by adding substances which are freely soluble in water, soluble in water, highly swelling or lipophilic.

6. A dosage form as claimed in claim 1, wherein the friability is less than 3%.

7. A dosage form as claimed in claim 1, wherein a water-soluble or water-insoluble, release-slowing coating is applied to the oral dosage form.

8. A dosage form as claimed in claim 5, wherein the highly swelling substances which are soluble in water are selected from the group consisting of alginates, pectins, galactomannans, carrageenans, dextran, curdlan, pullulan, gellan, chitin, gelatin, xanthans, hemicelluloses, cellulose derivatives, starch derivatives, and derivatives thereof, and the lipophilic substances are selected from the group consisting of fatty alcohols, fatty acids, and lipophilic polymers.

9. A dosage form as claimed in claim 8, wherein the highly swelling substances which are soluble in water are selected from the group consisting of methylcellulose, hydroxypropylmethylcellulose, hydroxypropylcellulose, hydroxyethylcellulose, carboxymethylcellulose, carboxymethyl starch, degraded starch, maltodextrins, polyacrylic acid, polymethacrylic acid, acrylic acid/methacrylic acid copolymers, polyvinyl alcohols, high molecular weight polyethylene glycols, polyoxyethylene/polyoxypropylene block copolymers, high molecular weight polyvinylpyrrolidones, and derivatives thereof.

10. A dosage form as claimed in claim 5, wherein the substances which are soluble in water are selected from the group consisting of polyethylene glycols, polyvinylpyrrolidone and vinylpyrrolidone/vinyl acetate copolymers.

11. A dosage form as claimed in claim 5, wherein the lipophilic substances are selected from the group consisting of stearyl alcohol, stearic acid, glycerides, fatty acid esters, fatty alcohol esters, ethylcellulose, cellulose acetate, acrylic ester/methacrylic ester copolymers, methacrylic acid/acrylic ester copolymers, cellulose acetate phthalate, cellulose acetate succinate, hydroxypropylmethylcellulose acetate phthalate, and hydroxypropylmethylcellulose acetate succinate.

12. A dosage form as claimed in claim 1, which comprises as other excipients c) lubricants, binders, disintegrants, flow regulators, stabilizers, colorants or bulking agents.

13. A dosage form as claimed in claim 1, which comprises as active ingredients a) food supplements or additives, vitamins, minerals or trace elements or active pharmaceutical ingredients.

14. A dosage form as claimed in claim 1, which comprises as active ingredients a) active pharmaceutical ingredients.

15. A dosage form as claimed in claim 1, wherein the active pharmaceutical ingredient is selected from the group consisting of benzodiazepines, antihypertensives, vitamins, cytostatics, anesthetics, neuroleptics, antidepressants, antibiotics, antimycotics, fungicides, chemotherapeutics, urologicals, platelet aggregation inhibitors, sulfonamides, spasmolytics, hormones, immunoglobulins, sera, thyroid therapeutics, psychopharmaceuticals, antiparkinson agents, other antihyperkinetics, ophthalmologicals, neuropathy products, calcium metabolism regulators, muscle relaxants, lipid-lowering agents, liver therapeutics, coronary agents, cardiac agents, immunotherapeutics, regulatory peptides, regulatory peptide inhibitors, hypnotics, sedatives, gynecologicals, antigout agents, fibrinolytics, enzyme products, transport proteins, enzyme inhibitors, emetics, perfusion promoters, diuretics, diagnostics, corticoids, cholinergics, biliary therapeutics, antiasthmatics, bronchiospasmolytics, beta-receptor blockers, calcium channel blockers, ACE inhibitors, arteriosclerosis remedies, antiinflammatory agents, anticoagulants, antihypotensives, antihypoglycemics, antifibrinolytics, antiepileptics, antiemetics, antidotes, antidiabetics, antiarrhythmics, antianemics, antiallergics, anthelmintics, analgesics, analeptics, aldosterone antagonists, and weight-reducing agents.

16. A dosage form as claimed in claim 1, wherein two or more layers are present and differ in the content of active ingredient and formulated mixture of polyvinyl acetate and polyvinylpyrrolidone.

17. A dosage form as claimed in claim 1, which is a press-coated tablet with a core with a very high active ingredient content.

18. A process for producing oral dosage forms as claimed in claim 1, which comprises tableting an initial mixture of the dosage form components using a pressure of less than 100 MPa.

19. A process for producing oral dosage forms as claimed in claim 18, wherein the initial mixture is tableted directly or the initial mixture or a part thereof is wet-granulated or dry-compacted before the tableting.

20. A drug product for delayed release of active ingredient, which is an oral dosage form as claimed in claim 1.

21. A process for producing drug products with delayed release of active ingredient for treating diseases, comprising incorporating the active ingredient into the oral dosage form as claimed in claim 1.

22. The process as claimed in claim 21, wherein the active ingredient is selected from the group consisting of food supplements, food additives, vitamins, minerals, trace elements, and active pharmaceutical ingredients.

* * * * *